United States Patent [19]
Yamato et al.

[11] 4,363,649
[45] Dec. 14, 1982

[54] APPARATUS FOR INSPECTION OF GLASS CONTAINERS

[75] Inventors: Yoshihiro Yamato; Kazuaki Ogawa, both of Yokohama; Hiromasa Satoh, Kawaguchi; Kiyoshi Chiku; Hideo Okada, both of Yokohama, all of Japan

[73] Assignee: Toyo Garasu Kabushiki Kaisha, Tokyo, Japan

[21] Appl. No.: 311,010

[22] Filed: Oct. 13, 1981

[51] Int. Cl.³ .............................................. C03B 35/04
[52] U.S. Cl. ....................................... 65/158; 65/165; 73/12
[58] Field of Search ....................... 65/158, 165; 73/12

[56] References Cited

U.S. PATENT DOCUMENTS

| | | | |
|---|---|---|---|
| 2,849,114 | 8/1958 | Noble et al. | 65/158 X |
| 3,702,563 | 11/1972 | Brady et al. | 73/12 |
| 3,999,420 | 12/1976 | Wright | 73/12 |

FOREIGN PATENT DOCUMENTS

1055768 4/1959 Fed. Rep. of Germany .
2617779 3/1977 Fed. Rep. of Germany .......... 73/12

*Primary Examiner*—Arthur D. Kellogg
*Attorney, Agent, or Firm*—Wenderoth, Lind & Ponack

[57] ABSTRACT

An impact rod is vertically guided within a guide cylinder to drop into a glass bottle to be tested which is held vertically below by a bottle gripper, the impact rod thereby striking the bottom of the bottle with preset impact force. A plurality of these guide cylinders with respective impact rods and corresponding bottle grippers are supported on structures revolving unitarily around a pole, the bottle grippers operating to grip successively bottles supplied from a production line and to carry the bottles around a partial circle as they are tested by the corresponding impact rods which are operated by adjustable cam action. The impact force is adjustably variable by adjusting the height of drop and/or weight of the impact rod.

4 Claims, 8 Drawing Figures

APPARATUS FOR INSPECTION OF GLASS CONTAINERS

BACKGROUND OF THE INVENTION

This invention relates generally to techniques for inspecting glass vessels or containers and more particularly to a glass container inspection apparatus installed in the production line of glass containers such as glass bottles and jars and adapted to cause an impact rod to drop freely from a specific height into each glass vessel thereby to test the strength of the bottom of that glass vessel.

During the production process of glass containers, cracks are sometimes formed in a part of the glass or gas bubbles or some other matter become mixed with the glass in some instances, and these defects remain in the glass until the containers are formed. Since the mechanical strength of glass containers having such defects tends to be low and is unreliable, it is necessary to carry out inspection of all glass containers at an intermediate point in their production line and to reject any which are found to have such defects. In order to carry out an inspection of this nature, it has been a common practice heretofore to introduce pressurized water into each glass container to be inspected through its mouth thereby to apply water pressure to the interior of the container to test its strength.

In this conventional testing method, however, the glass container must be filled with pressurized water, whereby an elaborate testing apparatus must be installed, and a long time is required for the test. For this reason, it is extremely difficult to apply a test of this nature with respect to each and every glass container on the production line, that is, to carry out a 100-percent inspection. Therefore, it has heretofore been unavoidably necessary to resort to spot-checking tests, whereby there has been the possibility of defective items existing in the lots of finished products.

Accordingly, in order to solve this problem, we have previously provided an apparatus (as disclosed in the specification of Japanese Patent Laid Open No. 129283/1976) for testing the strength of glass containers by causing a rod to descend toward the bottom of each vessel through the mouth thereof so that its lower tip abuts against the center of the bottom surface of the container thereby to apply a static load to the bottom surface.

However, this previous apparatus for testing glass containers was still inadequate for actual use in combination within a production line for continuously producing glass containers in large quantity. More specifically, in order to reduce a glass container inspection apparatus to practice, the glass container strength test must be carried out continuously in an intermediate part of the glass container production line. Furthermore, the apparatus must be made adjustable in accordance with the dimensions, particularly the height or depth, of the glass containers being produced.

SUMMARY OF THE INVENTION

It is an object of this invention to provide a glass container inspection apparatus which is combined within a glass container production line, and in which are used impact rods capable of easily testing all glass containers being continuously produced.

According to this invention, briefly summarized, there is provided an apparatus for inspection of glass containers comprising:

a center pole fixedly and vertically supported on a fixed base;

a horizontal circular table integrally and coaxially joined to the upper part of a hollow cylindrical table pedestal fitted loosely and coaxially around the middle part of the center pole and rotatably supported to revolve thereabout;

driving means for driving the table pedestal in revolution;

a rim-surface cam fixed coaxially to the upper part of the center pole and comprising a vertical hollow cylinder with an upper rim surface forming an endless cam surface;

a guide ring disposed coaxially relative to the rim-surface cam and adapted to revolve unitarily with the circular table;

a plurality of guide cylinders fixedly supported in upright state on the guide ring at equal spacing intervals therearound;

an impact rod assembly having an impact rod and accommodated in a freely droppable manner within each guide cylinder;

container grippers supported on the circular table to revolve unitarily therewith and operating, as the table is revolved, to successively grip respective glass containers to be inspected supplied in succession thereto from a production line, to carry the containers in a partially circular path as each container gripper holds upright its respective container in the drop path of a respective one of the impact rods, to release and reject the container if it fails to pass the inspection, and to return the container to the production line if it passes the inspection;

a sector disposed on the inner side of the rim-surface cam and adapted to adjustably set the height of drop of the impact rod;

first and second follower means rotatably supported on a cantilever cross pin fixed perpendicularly to each impact rod assembly, the first and second follower means being adapted to roll respectively along the sector and the cam surface, the first follower means rolling off a downstream end of the sector to permit the impact rod assembly to drop thereby to cause the lower end of the impact rod to strike against the inner side of the bottom of the corresponding container with a preset impact energy; and control means including a detection device for detecting any abnormal dropping motion of each impact rod through the bottom of a defective container, the control means thereupon causing the container gripper holding that container to release and reject the same.

In accordance with this invention, a strength test is carried out on each glass container to be inspected by causing an impact rod to fall freely from a specific height into the glass container and thus applying an impact force to the bottom of the container. Accordingly, by merely adjustably setting the height of drop and/or the weight of the impact rod, strength tests of glass containers of various dimensions, shapes, and other characteristics can be carried out. Furthermore, a plurality of impact rods are held in a guided droppable manner on the rotating guide ring, and, in combination with the rim-surface cam and the drop height adjusting sector, the drop height and/or weight of each impact rod can be adjustably set as required. Therefore, by installing the apparatus of this invention in combination in the production line of glass containers, 100-percent testing of the glass containers can be readily carried out.

The nature, utility, and further features of this invention will be apparent from the following detailed description with respect to a preferred embodiment thereof when read in conjunction with the accompanying drawings briefly described below. The example of the glass container inspection apparatus described hereinbelow is particularly adapted for the inspection of glass bottles.

DETAILED DESCRIPTION OF THE INVENTION

Figure 1:
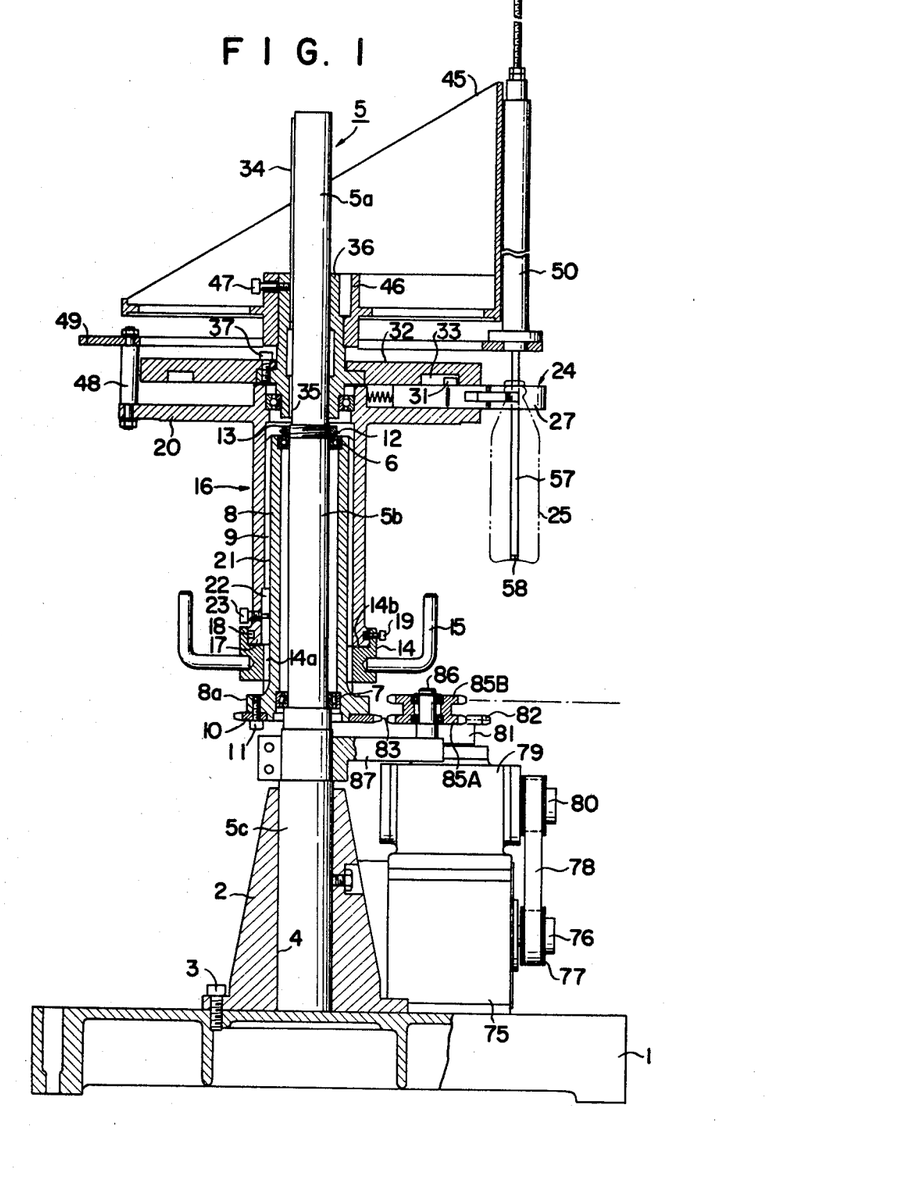
FIG. 1 is an elevation, with some parts shown in vertical section, showing the essential parts of one example of practice of the glass container inspection apparatus according to this invention.

Referring first to FIG. 1, the example of a glass bottle inspection apparatus illustrated therein has a fixed base 1 on which the other parts of the apparatus are supported. A pedestal-like bracket 2 having a vertical pole-receiving bore 4 is fixed by bolts 3 on the base 1 near the central part thereof. The lower end of a center pole 5 having an upper part 5a, a middle part 5b, and a lower part 5c if fitted in the pole-receiving bore 4 of the bracket 2 and is fixed against rotating by suitable means such as a locking bolt.

Around the middle part 5b of the center pole 5, there is coaxially disposed a sleeve 8 rotatably supported at its upper and lower ends by an upper bearing 6 and a lower bearing 7 on the middle part 5b. This sleeve 8 is provided on and around its outer surface with external screw threads 9 of trapezoidal shape in section and has a flange 8a at its lower end. A driven sprocket 10 is fixed by screws 11 to the lower face of the flange 8a in coaxial alignment therewith.

The inner race of the upper bearing 6 is retained by a lock washer 12 and a tightening nut 13 in screw engagement with screw threads formed on the outer surface of the upper end of the middle pole part 5b. The inner race of the lower bearing 7, which functions partly as a thrust bearing, rests on an upwardly-facing annular ledge or shoulder formed around the lower end of the middle pole part 5b, while the outer race of the lower bearing 7 is in abutting contact with a downwardly-facing annular ledge formed around the inner surface of the lower end of the sleeve 8. Accordingly, the sleeve 8 is rotatable about the center pole 5 but is restricted from moving in the axial direction.

The above mentioned external screw threads 9 of the sleeve 8 are meshed with internal screw threads 14a of a height-adjusting ring 14, which, in the state shown in FIG. 1, is disposed at the lower end of the sleeve 8. The height-adjusting ring 14 can be raised or lowered by rotating it by means of handles 15 fixed thereto around the periphery thereof.

A table assembly comprising essentially a table pedestal 16 of cylindrical shape and a circular table 20 formed integrally with the table pedestal 16 at the upper part thereof is disposed coaxially around the sleeve 8 with a clearance therebetween. A seating ring 17 formed coaxially and integrally with the lower end of the table pedestal 16 is seated on an annular seat surface 14b formed on the upper part of the above described height-adjusting ring 14, the seating ring 17 fitting into an annular, socket-like recess formed by the seat surface 14b and an annular, cylindrical rim projecting upwardly from the outer periphery of the height-adjusting ring 14. The upper part of the table assembly is rotatably connected and coaxially centered by means of bearings to a holding cylinder 36 described hereinafter.

The above mentioned seating ring 17 at the lower end of the table pedestal 16 is provided with an outwardly opening annular groove 18, into which one or more holding screws 19 are projected through the above mentioned cylindrical rim on the upper part of the height-adjusting ring 14 so that their tips are pressed against the bottom of the groove 18. Rotation of the sleeve 8 and the table pedestal 16 relative to each other is prevented by a key 22 which is inserted in a key slot 21 formed in the outer side of the sleeve 8 parallelly to the axial direction thereof and is held on the side of the table pedestal 16 by a holding screw 23 screwed from the outside through a tapped hole in the table pedestal 16 near its lower end.

Figure 2:
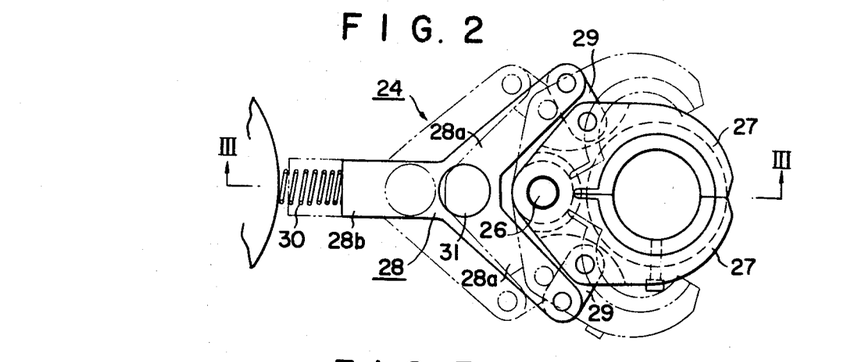
FIG. 2 is a relatively enlarged plan view of a container gripper.
Figure 3:
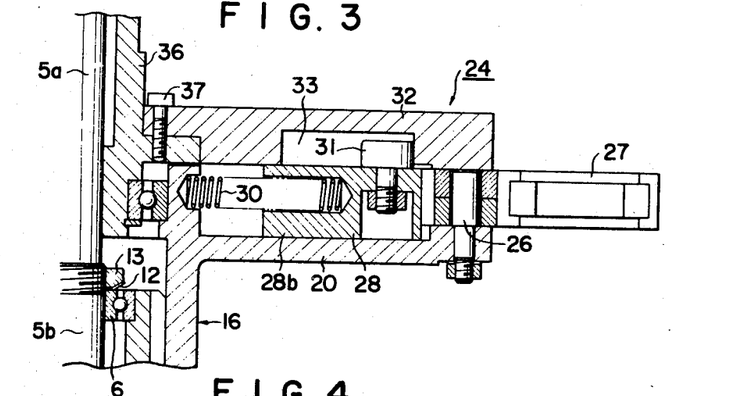
FIG. 3 is a section taken along the plane indicated by line III—III in FIG. 2 as viewed in the arrow direction.

The above mentioned circular table 20 supports on its upper surface eight bottle grippers 24, 24, . . . 24 arranged on and around a common circle at equal intervals and adapted to revolve together with the table as they firmly grip and subsequently release the neck parts of respective glass bottles 25. As shown in FIGS. 2 and 3, each bottle gripper 24 has a pair of gripping jaws 27, 27 pivoted at their inner ends in an openable and closable manner by a common pivot pin 26 secured to the table 20. Each of these gripping jaws 27, 27 is linked by a pin-connected link 29 to the outer end of a respective one of two yoke arms 28a, 28a of a Y-shaped push-pull member 28. Thus, the gripping jaws 27, 27 are closed and opened by the pushing and pulling movements of the push-pull member 28 in the axial direction of its shank 28b.

Each push-pull member 28 is continually urged to move outward in the "push" direction by a compression spring 30 abutting at its outer end against the inner end of the shank 28b of the push-pull member 28. Furthermore, a cam follower 31 is fixed to the common root part of the yoke arms 28a, 28a of each push-pull member 28 as best shown in FIG. 3. As described more fully below, this cam follower 31 is adapted to be pressed against the outer peripheral surface 33a of an annular cam groove 33 of a cam disk 32.

Figure 4:
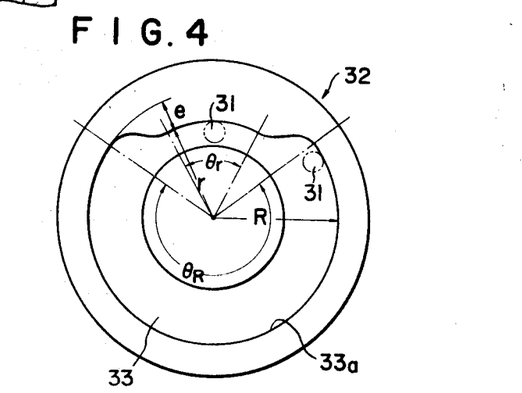
FIG. 4 is a bottom view showing a cam groove of a cam disk.

As shown in FIG. 1, this cam disk 32 is positioned coaxially above the table 20 and is supported on and fixed by bolts 37 to the aforementioned holding cylinder 36. The holding cylinder 36 is fixedly secured by way of keys 34 and 35 to the upper part 5a of the center pole 5. As shown in FIG. 4, the cam disk 32 has a substantially annular groove 33, whose outer wall surface 33a constitutes a cam surface comprising a relatively longer region $\theta_R$ of a radius R, a shorter region $\theta_r$ of a radius r, and regions of transition therebetween. When the cam follower 31 is following the cam surface in the region $r \cdot \theta_r$ of the shorter radius r, it is causing the push-pull member 28 to be retracted by a distance $e = R - r$, whereby the gripping jaws 27, 27 are in their fully opened state. When the cam follower 31 is traveling along the region $R \cdot \theta_R$ of the longer radius R, the gripping jaws 27, 27 are in their closed state.

The mechanical section of the apparatus which successively holds, by means of the bottle grippers 24, 24, . . . 24, the glass bottles 25, 25, . . . 25 to be inspected within the production will now be described with reference to FIG. 5.

Bottles 25, 25, . . . 25 to be tested are successively conveyed in single file on a conveyor 38 in the production line toward an entrance star wheel 39, the spacing intervals between the bottles being regulated to a specific uniform pitch by an infeed worm device 40 before the bottles reach the entrance star wheel 39. The bottles 25, 25, . . . 25 are thus successively fed to the entrance star wheel 39 and are successively engaged by the arcuately curved surfaces of receiving concavities 39a, 39b, 39c, and 39d of the entrance star wheel 39, which successively brings the bottles into the circular path of the bottle grippers 24, 24, . . . 24 to be successively gripped thereby and tested as described hereinafter.

The bottles which have been tested are taken out of the path of the bottle grippers 24, 24, . . . 24 by an exit star wheel 41 positioned symmetrically opposite to the entrance star wheel 39 with respect to the table 20 and the center pole 5. This exit star wheel 41 is of substantially the same shape as the entrance star wheel 39, having receiving concavities 41a, 41b, 41c, and 41d.

Referring again to FIG. 1, a cylindrical rim-surface cam 45 is fixed at its boss 46 by at least one bolt 47 to the upper part of the aforementioned holding cylinder 36, thereby being fixed against rotation. As indicated by the development diagram of FIG. 6 and in FIG. 7, this rim-surface cam 45 has a cam surface comprising a steeply declining surface 45A, a gently inclining surface 45B of opposite slope direction, and a flat drop-bottom surface 45C therebetween.

Figure 7:
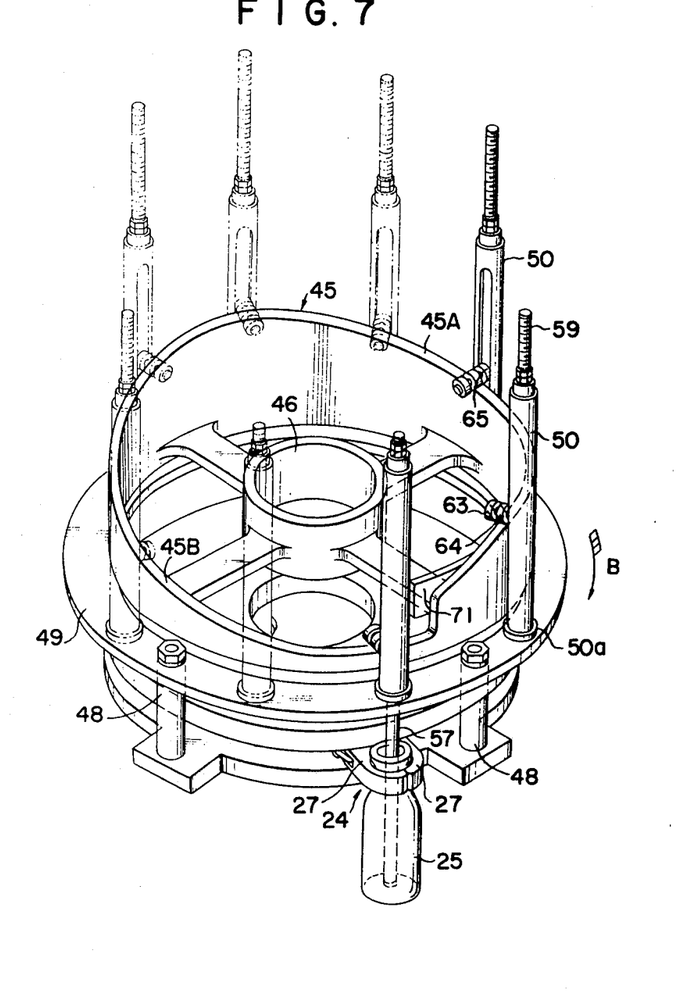
FIG. 7 is a perspective view showing essential parts of a device for causing impact rods to undergo free drops.
Figure 8:
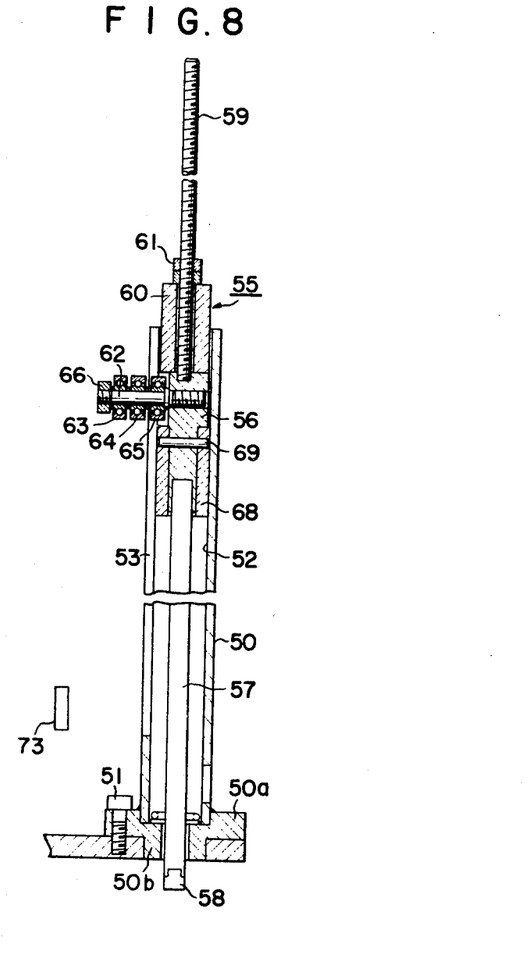
FIG. 8 is an elevation, with some parts shown in vertical section, showing an impact-rod assembly.

The circular table 20 fixedly supports at its peripheral part a plurality of vertical support columns 48, 48, . . . 48, which support in turn at their upper ends an annular guide ring 49. As best shown in FIG. 7, this guide ring 49 supports on its upper surface eight vertical guide cylinders 50, 50, . . . 50 positioned at equal intervals around a common circle. Each guide cylinder 50 has a flange 50a near its lower end which is secured to the guide ring 49 by at least one bolt 51 as shown in FIG. 8. Integrally and coaxially formed with the flange 50a is a downwardly projecting cylindrical portion 50b, which is fitted in a through hole in the guide ring 49. This cylindrical portion 50b has a central bore in which the lower end of an impact rod 57, described hereinbelow, is slidably fitted to be guided thereby. Furthermore, each guide cylinder 50 has a guide bore 52 and a guide slot 53 formed in the longitudinal or vertical direction through its wall on its side facing the center pole 5.

Within each guide cylinder 50, an impact rod assembly 55 described in detail hereinbelow is loosely fitted so that it can freely drop when it is released from a specific raised position. Each of the eight guide cylinders 50, 50, . . . 50 accommodating a respective impact rod assembly 55 is so positioned relative to a respective one of the eight bottle grippers 24, 24, . . . 24 that the impact rod of that impact rod assembly 55 will be vertically and coaxially alined with a bottle gripped by the gripping jaws 27, 27 of that respective one bottle gripper 24.

As shown in FIG. 8, each impact rod assembly 55 has a connector 56, to the lower end of which the upper end of a downwardly extending impact rod 57 is connected. A striking head 58 is fixed to the lower end of the impact rod 57. A screw-threaded rod 59 extending upward is connected at its lower end to the upper part of the connector 56. A variable weight 60 is loosely fitted around the threaded rod 59 at the lower part thereof and rests on the upper surface of the connector 56, being tightly secured in place by double nuts 61 thread-engaged with the threaded rod 59.

The variable weight 60 is so adapted that its weight can be freely varied thereby to adjust the impact energy imparted to a glass bottle to be tested to a value suitable for that bottle. For this purpose, the weight 60 may be one of a series of weights of respectively different weight values, or it may be composed of washer-like independent rings of suitable number and weight values with extra rings prepared for increasing the total weight value.

A horizontal cross pin 62 is screwed at its one end into a tapped hole in the connector 56 near the upper end thereof and extends toward the center pole 5 in the form of an axle. On this axle portion of the cross pin 62, first and second follower wheels 63 and 64 and a guide wheel 65 are rotatably supported in slightly spaced-apart state in sequence, the first guide wheel 63 being the outermost. These wheels are held in place by a nut 66 screwed onto the axle portion at its outer end. Of these wheels, the guide wheel 65 is adapted to roll in the aforementioned guide slot 53 of the guide cylinder 50. Roller or ball bearings are advantageously used for these wheels 63, 64, and 65.

Furthermore, a detection cylinder 68 is fitted around the lower part of the connector 56 and is held in place by a transverse pin 69. In addition, a defective bottle detection sensor 73 for detecting any abnormally excessive drop of the impact rod 57 is disposed beside each guide cylinder 50 as shown in FIG. 8. The detection sensor 73 is preferably a magnetic proximity switch for detecting approach of the nut 66.

The second follower wheel 64 on the axle portion of the cross pin 62 of each impact rod assembly 55 is adapted to roll on and along the cam surface of the aforedescribed rim-surface cam 45 and, by following the variations in the heights of the cam surfaces 45A and 45B, to vary the height of the impact rod assembly 55. As shown in FIGS. 5 and 6, a drop height adjusting sector 71 is mounted on one part of the inner cylindrical surface of the rim-surface cam 45. The first follower wheel 63 on the axle part of the cross pin 62 is adapted to roll on and along the upper surface of this drop height adjusting sector 71. As will be apparent from FIG. 6, this height adjusting sector 71 is provided in a position to intersect the steep surface 45A of the rim-surface cam 45 as viewed from the side and is so adapted that its height can be freely adjusted between a maximum height position X and a minimum height position Y.

Next, the driving mechanism of the table pedestal 16 and the circular table 20 will be described. Referring again to FIG. 1, a driving motor 75 is mounted on the base 1, and a timing gear 77 is connected to its output shaft 76. The rotation of this timing gear 77 is transmitted by way of a timing belt 78 to a timing gear 80 on the input shaft side of a speed-reducing mechanism 79. On the output shaft 81, of the speed-reducing mechanism 79, a sprocket 82 is fixedly mounted. This sprocket 82 and the aforementioned driven sprocket 10 are coupled by a chain 83 for transmission of motive power to the driven sprocket 10.

One of the spans of the chain 83 between the sprockets 10 and 82 is meshed with a driven sprocket 85A for applying tension to the chain 83 and for taking off rotational power therefrom. This sprocket 85A is integrally and coaxially formed on a common boss with another sprocket 85B disposed above and slightly apart from the sprocket 85B. This double sprocket 85A, 85B is rotatably supported on a vertical axle 86 which in turn is fixedly supported by an arm 87 fixed to and extending outwardly from the center pole 5.

The sprocket 85B is coupled by a chain 92 to a driven sprocket 90 coaxially and integrally fixed to the aforedescribed entrance star wheel 39 and to a driven sprocket 91 coaxially and integrally fixed to the exit star wheel 41. The chain 92 thereby assumes a triangular form and is tensioned by a tension sprocket 93 meshed therewith in the span thereof between the sprockets 85B and 90.

The example of an apparatus for inspection of glass containers of the above described construction and organization according to this invention operates as follows.

Figure 5:
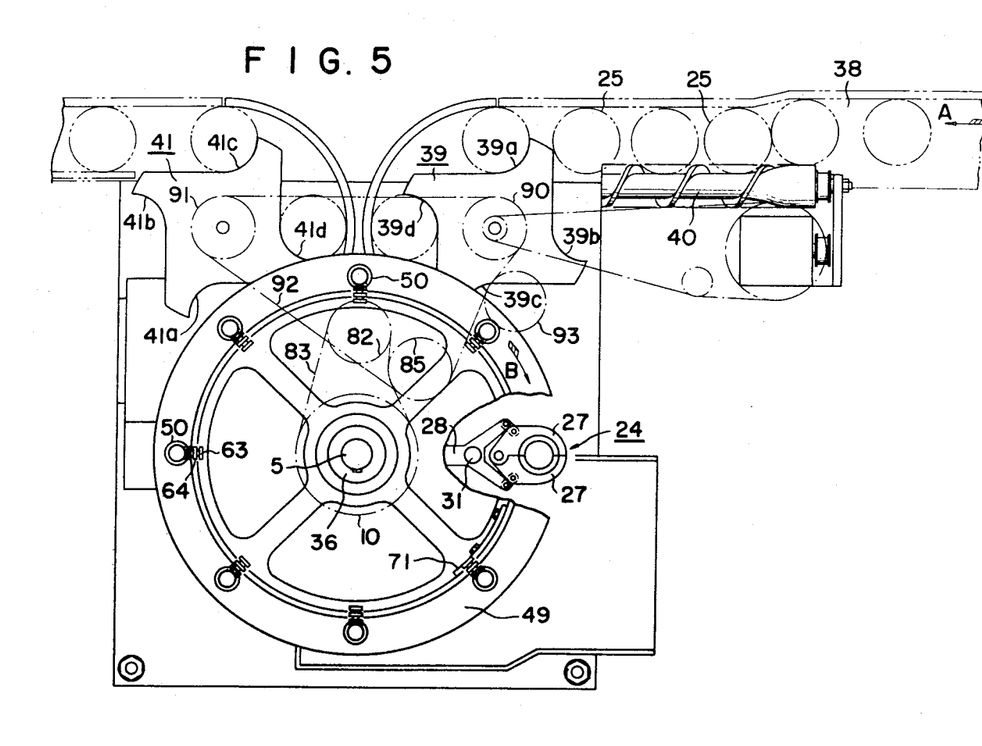
FIG. 5 is a plan view of the glass container inspection apparatus.
Figure 6:
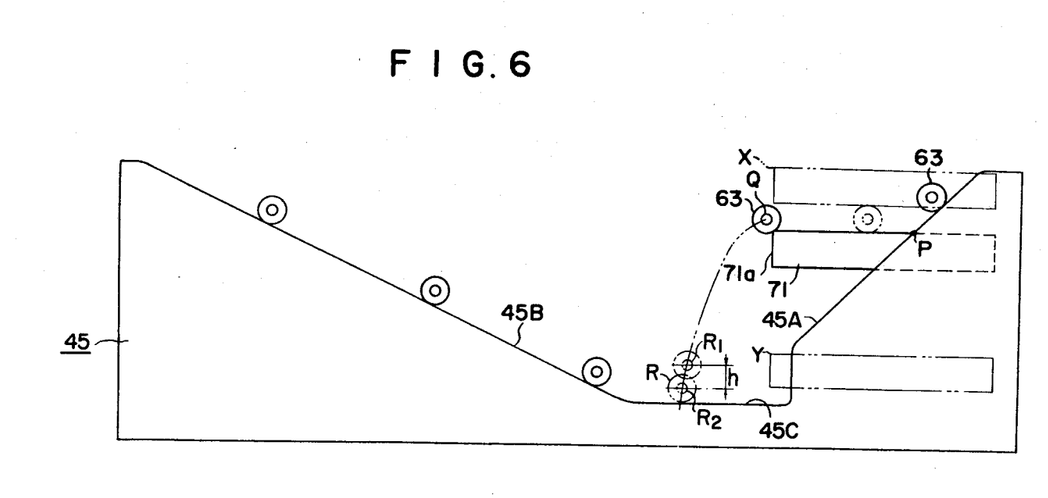
FIG. 6 is a diagram indicating the relationship between the development of the cam surface of a rim-surface cam and a height-adjusting sector.

Referring to FIG. 5, the glass bottles to be inspected are conveyed in single file by the conveyor 38 in the arrow direction A toward the entrance of the apparatus and, after their pitch or spacing has been regulated by the infeed worm device 40, are successively engaged by the curved surfaces of the receiving concavities 39a, 39b, 39c, and 39d of the revolving entrance star wheel 39. The bottles are thus revolved in the counterclockwise direction as viewed in FIG. 5, and each bottle in turn is supplied to a respective one bottle gripper 24 on the revolving table 20 and is gripped at the upper part of its neck by the gripping jaws 27, 27 of that bottle gripper.

During the normal operation of the inspection apparatus, the table pedestal 16, the table 20, the guide ring 49, the bottle grippers 24, 24, . . . 24, the impact rod assemblies 55, 55, . . . 55, and other parts are revolving unitarily in the clockwise direction of arrow B in FIG. 5.

In the meantime, the second follower wheel 64 of the impact rod assembly 55 vertically alined with the bottle gripper 24 to which a bottle has been supplied as described above has rolled along the cam surface 45A and 45B of the rim-surface cam 45 and reaches the intersection P as shown in FIG. 6 between the upper surface of the height-adjusting sector 71 and the steeply declining surface 45A. At this point, the first follower wheel 63 rides onto the upper surface of the height-adjusting sector 71, and thereafter the impact rod assembly 55 revolves and advances in the arrow direction B with the height of the impact rod 57 maintained constant as determined by the height adjusting sector 71.

Then, when the first follower wheel 63 reaches and passes the downstream end 71a of the sector 71, it loses its support surface and freely drops along a drop path Q–R toward the drop bottom surface 45C. Simultaneously, the impact rod 57 also freely drops into the glass bottle 25 which is being gripped by the corresponding bottle gripper 24, and the striking head 58 collides with the center of the bottom of the bottle 25, thereby imparting impact energy to the bottle bottom.

As a result, in the case where there is no abnormality or defect in the bottle bottom, the impact rod 57 is held in the state wherein it has struck and abutted against the bottle bottom. In the case where the bottle bottom has a low strength because of cracks, air bubbles, or some other defect therein, however, the bottle bottom breaks away and drops, whereby the impact rod 57 drops further than normally.

In FIG. 6, reference character $R_1$ designates the lowest point to which the first follower wheel 63 drops in the case of a bottle without defects, while reference character $R_2$ designates its lowest drop point in the case of a defective bottle. In the case of a defective bottle, the difference h is detected by the aforedescribed defective bottle detection sensor 73, which immediately indicates the presence of the defective bottle and transmits a corresponding signal to controlling means (not shown), which causes the bottle gripper 24 gripping that defective bottle to release the same at a suitable position, the defective bottle thereby being rejected and dropped into a chute (not shown) for removal from the line. Bottles without defects are revolved and, after being released by their bottle grippers upon reaching the exit star wheel 41, are guided by the exit star wheel 41 onto a conveyor and thus sent to a succeeding process step.

While this invention has been described above with respect to a specific example of a glass bottle inspection apparatus, it is to be understood that this invention is not thus limited but may be applied also for inspection of a wide range of other glass containers.

What we claim is:

1. An apparatus for inspection of glass containers comprising:
   a horizontal circular table revolvably supported to revolve about a vertical axis;
   a guide ring disposed coaxially above and spaced apart from the circular table and joined integrally thereto to be revolvable unitarily therewith;
   driving means for driving the table;
   a rim-surface cam fixedly supported and comprising a vertical hollow cylinder disposed coaxially with the guide ring and having an upper rim surface forming an endless cam surface;
   a plurality of guide cylinders fixedly supported in upright state on the guide ring at equal spacing intervals therearound;
   an impact rod assembly having an impact rod and accommodated in a freely droppable manner within each guide cylinder;
   container grippers supported on the table at equal intervals therearound to revolve unitarily therewith and operating, as the table revolves, to successively grip respective glass containers to be inspected supplied in succession thereto from a production line, to carry the containers in a partially circular path as each container gripper holds upright its respective container in the drop path of a respective one of the impact rods, to release and reject the container if it fails to withstand impact by that impact rod, and to return the container, if thus withstands impact, to the production line;

a sector adjustably supported on the inner side of the rim-surface cam to adjustably set the height of drop of the impact rod;

first and second follower means rotatably supported on each impact rod assembly and adapted to travel respectively along the sector and the cam surface, the first follower means moving off a downstream end of the sector to permit the impact rod assembly to drop thereby to cause the lower end of the impact rod to strike against the inner side of the bottom of the corresponding container with a preset impact energy; and control means including a detection device for detecting any abnormal dropping motion of each impact rod due to breakage or dropping out of the bottom of a defective container, the control means thereupon causing the container gripper holding that container to release and reject the same.

2. An apparatus according to claim 1 in which the circular table is integrally and coaxially joined to the upper part of a hollow cylindrical table pedestal fixedly supported at its lower end on a height-adjusting ring having internal screw threads meshed with external screw threads formed around the outer cylindrical surface of a sleeve which is coaxially and partly enclosed within the table pedestal with clearance therebetween and rotatably and coaxially supported on the middle part of a center pole fixedly supported on a fixed base and extending upward through openings in the table and the guide ring, the height of the table pedestal being adjustable by rotating the height-adjusting ring relative to the sleeve, the rim-surface cam being fixedly and coaxially supported on the upper part of the center pole, means being provided to prevent relative rotation between the table pedestal and the sleeve and to permit relative axial movement therebetween.

3. An apparatus according to claim 1 in which the cam surface of the rim-surface cam comprises a steeply declining surface, a gently inclining surface of opposite slope direction, and a flat drop-bottom surface therebetween.

4. An apparatus according to claim 1 in which each impact rod assembly comprises: the impact rod coaxially disposed within the vertical guide cylinder; a connector fixedly and coaxially connected at its lower end to the upper end of the impact rod; an upper rod fixedly and coaxially connected at its lower end to the upper end of the connector; a weight of interchangeably variable mass detachably secured to the upper rod; a cantilever cross pin imbeddedly fixed at its proximal end to the connector and extending horizontally and out of the guide cylinder through a vertical slot formed therein, the cross pin being movably engaged with the vertical rims of the slot; and the first and second follower meams respectively comprising rollers rotatably supported on the cross pin at its part extending outside of the guide cylinder.

* * * * *